United States Patent [19]
Donahue et al.

[11] Patent Number: 5,601,583
[45] Date of Patent: Feb. 11, 1997

[54] SURGICAL INSTRUMENT

[75] Inventors: John R. Donahue, Pottstown, Pa.; Graham Smith, Plaistow, N.H.

[73] Assignee: Smith & Nephew Endoscopy Inc., Andover, Mass.

[21] Appl. No.: 388,992

[22] Filed: Feb. 15, 1995

[51] Int. Cl.$^6$ ..................................................... A61B 17/00
[52] U.S. Cl. .......................... 606/170; 606/171; 606/180; 604/22
[58] Field of Search ..................................... 606/170, 171, 606/180; 128/751–755; 604/22; 30/29.5, 276, 347

[56] References Cited

U.S. PATENT DOCUMENTS

| | | |
|---|---|---|
| 3,618,611 | 11/1971 | Urban . |
| 4,071,030 | 1/1978 | Hedrick . |
| 4,111,208 | 9/1978 | Levenberger ............................ 606/180 |
| 4,167,943 | 9/1979 | Banko . |
| 4,167,944 | 9/1979 | Banko . |
| 4,203,444 | 7/1987 | Bonnell et al. . |
| 4,274,414 | 6/1981 | Johnson et al. . |
| 4,522,206 | 6/1985 | Whipple et al. . |
| 4,649,919 | 3/1987 | Thimsen et al. . |
| 4,662,371 | 5/1987 | Whipple et al. . |
| 4,705,038 | 11/1987 | Sjostrom et al. . |
| 4,728,319 | 3/1988 | Masch ....................................... 604/22 |
| 4,811,734 | 3/1989 | McGurk-Burleson et al. . |
| 4,834,729 | 5/1989 | Sjostrom . |
| 4,842,578 | 6/1989 | Johnson et al. . |
| 4,844,064 | 7/1989 | Thimsen et al. . |
| 4,850,354 | 7/1989 | McGurk-Burleson et al. . |
| 4,867,157 | 9/1989 | McGurk-Burleson et al. . |
| 5,007,917 | 4/1991 | Evans . |
| 5,084,052 | 1/1992 | Jacobs . |
| 5,112,299 | 5/1992 | Pascaloff . |
| 5,152,744 | 10/1992 | Krause et al. . |
| 5,217,479 | 6/1993 | Shuler . |
| 5,275,609 | 1/1994 | Pingleton et al. ...................... 606/170 |
| 5,282,821 | 2/1994 | Donahue . |
| 5,320,635 | 6/1994 | Smith . |
| 5,376,078 | 12/1994 | Dinger, III et al. . |

FOREIGN PATENT DOCUMENTS

| | | |
|---|---|---|
| 0393834 | 10/1990 | European Pat. Off. . |
| 0445918A1 | 9/1991 | European Pat. Off. . |
| 0481760A1 | 4/1992 | European Pat. Off. . |
| 0609084 | 8/1994 | European Pat. Off. . |
| 0613661 | 9/1994 | European Pat. Off. . |
| 3828478A1 | 5/1989 | Germany . |

*Primary Examiner*—Michael Powell Buiz
*Assistant Examiner*—William Lewis
*Attorney, Agent, or Firm*—Fish & Richardson P.C.

[57] ABSTRACT

A surgical instrument includes a support member that extends distally from a base, carrying at a distal region a window defining an opening. A surgical tool at least partially disposed in the distal region is movable with respect to the window to cut tissue extending through the opening. A shield also at least partially disposed in the distal region is movable with respect to the window to at least partially cover the opening.

30 Claims, 8 Drawing Sheets

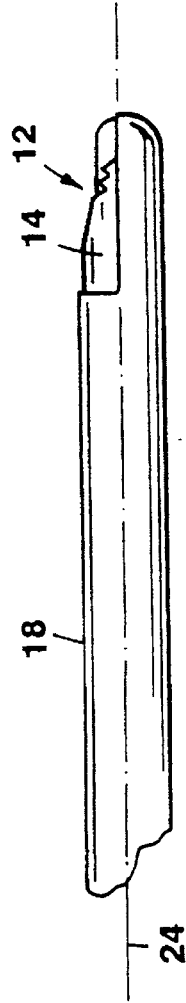
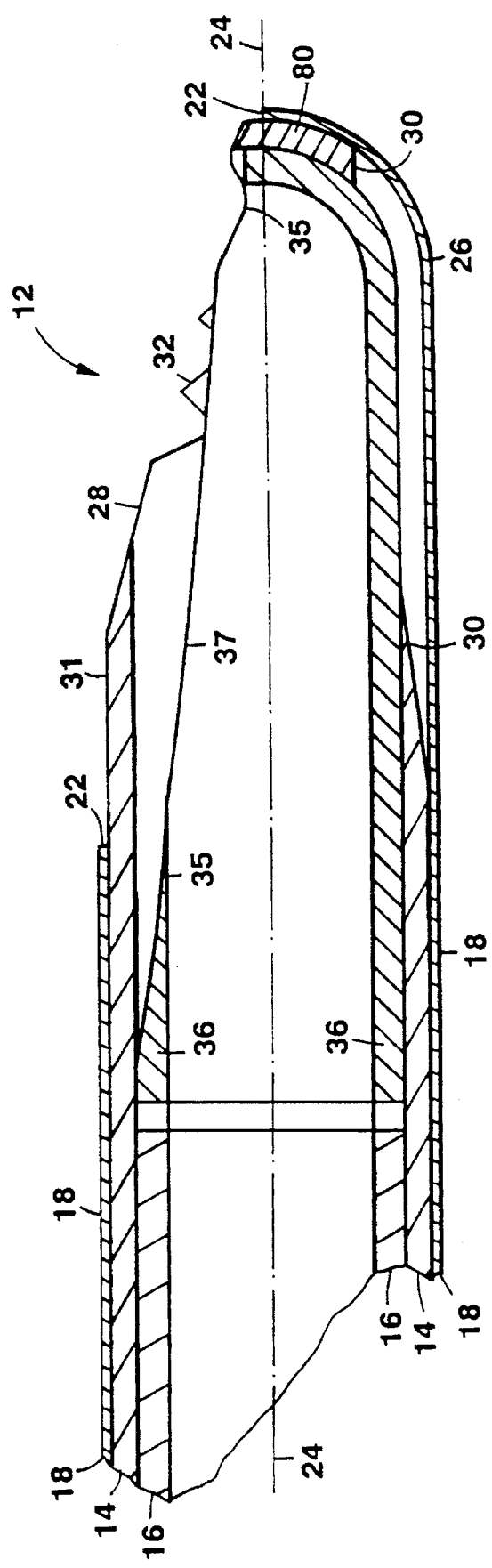

SURGICAL INSTRUMENT

BACKGROUND OF THE INVENTION

This invention relates to surgical instruments, and in particular to powered arthroscopic surgical instruments.

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all of which are assigned to the present assignee.

Some arthroscopic surgical instruments are linear, that is, straight between their proximal and distal ends. Others are curved to facilitate positioning the cutting implement against tissue to be cut without requiring that the instrument be removed from the body and reinserted through an additional puncture. In a curved instrument, a region of the inner tube is flexible to enable the inner tube to accept the curvature imposed by the outer tube while transmitting the torque applied by the motor to the blade.

SUMMARY OF THE INVENTION

One general aspect of the invention is a surgical instrument in which a movable shield can be positioned to at least partially cover the distal opening in a support member. Another general aspect of the invention is a method for using the surgical instrument. In still another general aspect, the support member has a pair of openings in its distal end, either of which can be selectively covered by the movable shield.

Among other advantages, the invention allows the user to partially or completely cover the opening by moving the shield, thereby preventing at least some tissue from entering into the instrument through the opening and being cut by the surgical tool. As a result, the cutting action of the surgical tool can be reduced or disabled by appropriate positioning of the shield.

Moreover, where the surgical instrument has a pair of openings at its distal end, the invention allows the user to partially or completely cover one of the openings by moving the shield, thereby preventing at least some tissue from entering into the instrument through that opening and being cut by the surgical tool. As a result, by appropriate positioning of the shield, the user can select between windows that have, for example, different cutting configurations and different rotational orientations.

For instance, one window can be configured for more aggressive cutting than the other. The preferred degree of cutting can thus be chosen by moving the shield to cover the opening of the window having the undesired cutting characteristics. Moreover, the windows may be located at different rotational orientations around the distal region of the support member. Thus, even if their cutting characteristics are identical, the windows can be selectively covered and uncovered to change the direction of cutting of the instrument.

Preferred embodiments include the following features.

In a particularly useful embodiment, an actuating member (e.g., a tube coaxially disposed outside the support member) extends distally from the base, and transmits a rotational force applied at a proximal end to move the shield, which is attached to a distal end of the actuating member. The proximal end of the actuating member is rigidly secured to a knob rotatably mounted to a stationary portion of the base. The knob may be selectively rotated to a plurality of discrete positions with respect to the base, allowing the shield to be positioned to a corresponding plurality of discrete rotational orientations. Because the actuating member is rotatably coupled to the base, the openings may be selectively covered and uncovered while the instrument remains in situ within the patient.

A drive member (e.g., a tube disposed coaxially within the support member) extends distally from the base, and transmits a rotational force applied at a proximal end to move at least a portion of the surgical tool, a cutting implement attached to a distal end of the drive member. As the drive member rotates, the edges of the cutting implement move toward and closely past the edges of the windows. A hollow passage in the tubular drive member is adapted to receive suction at its proximal end, transporting body material cut by the cutting implement away from a surgical site while the instrument remains in situ for further cutting.

The support member (e.g., a tube) couples to the base in a manner that allows it to slide axially with respect to the base. During assembly, the support tube is inserted into the actuator tube, and the actuator tube is attached to the base. When the drive tube is then inserted into the support tube, the outer surface of the distal tip of the drive tube bears against the inner surface of the distal tip of the support tube. Because the support tube can slide axially with respect to the base, this forces the support tube distally until the outer surface of the distal tip of the support tube bears against the inner surface of the distal tip of the actuator tube. Thus, when assembled, there is little or no gap between the distal tips of the various tubes. This reduces the amount of severed tissue, fluid, and other material that would otherwise pass into the annular regions separating the three tubes.

In alternate embodiments of the present invention, the support tube is bent, and an actuating member extending distally from the base is relatively flexible at least in the bend region, allowing the actuating member to transmit force through the bend region to move the shield. For instance, the actuating member (e.g., a tube disposed outside the support member) and the drive tube may both be relieved with a series of axially spaced slots in the region of the bend. This arrangement provides the actuating and drive tubes with the requisite transverse flexibility to accommodate the bend, and the necessary torsional stiffness to rotate the shield and the cutting implement, respectively. Because it is bent, the instrument may be used to operate on surgical areas that would otherwise be difficult to reach with a straight-shafted instrument.

In other embodiments, a relatively rigid sheath is disposed coaxially with, and is axially slidable with respect to, the bent support member, which is relatively deformable at least in the bend region. By sliding the rigid sheath fore and aft along the support member to selectively cover and uncover the bend region, a surgeon may change the angle of offset provided by the bend region, all while the instrument remains in situ within the patient.

Other features and advantages of the invention will become apparent from the following detailed description, and from the claims.

BRIEF DESCRIPTION OF THE DRAWINGS

FIG. 3 is a side view of the surgical instrument, taken along line 3—3 of FIG. 1.

FIG. 4 is a cross-sectional side view of a distal region of the surgical instrument.

DESCRIPTION OF THE PREFERRED EMBODIMENTS

Figure 1:
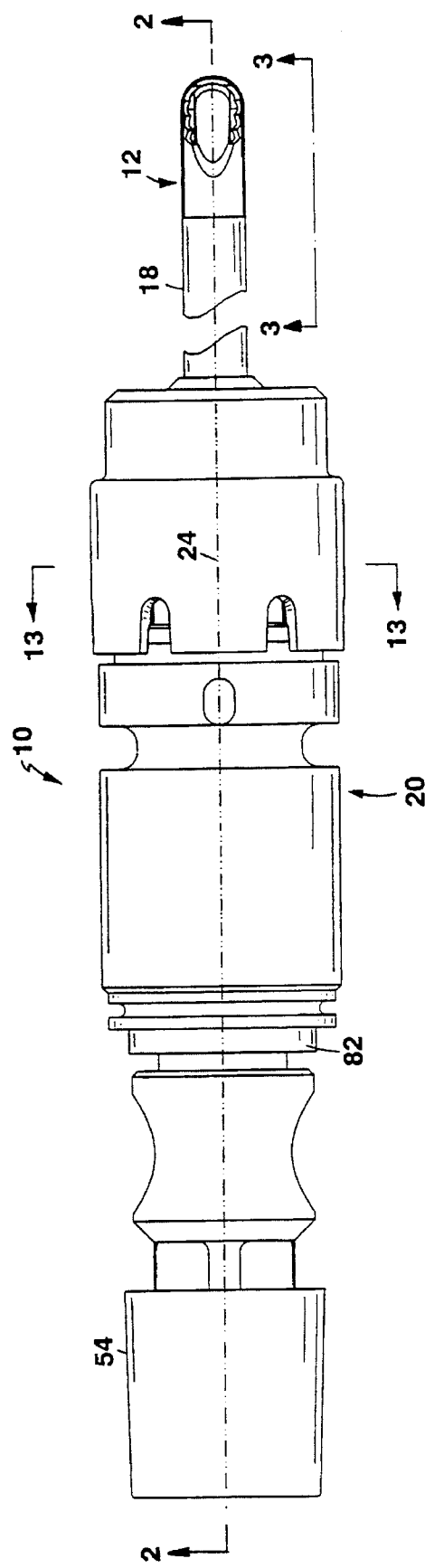
FIG. 1 is a top view of a surgical instrument.
Figure 2:
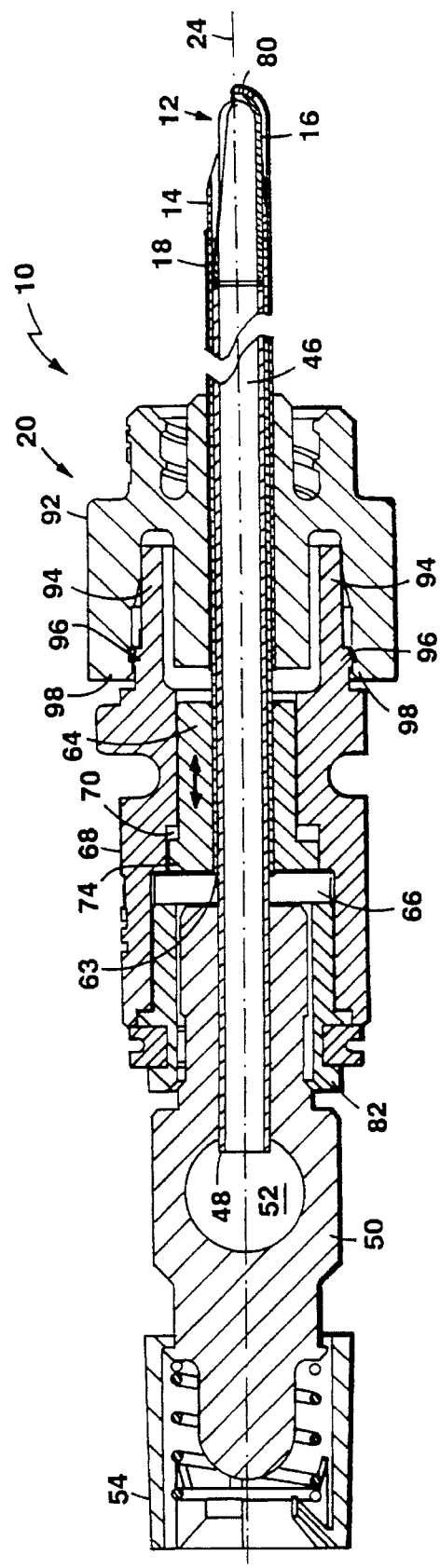
FIG. 2 is a sectional side view of the surgical instrument, taken along line 2—2 of FIG. 1.
Figure 5:
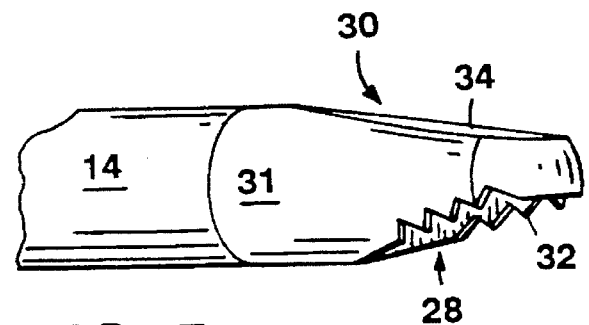
FIG. 5 is a perspective view of a distal region of the intermediate tube of the surgical instrument.
Figure 6:
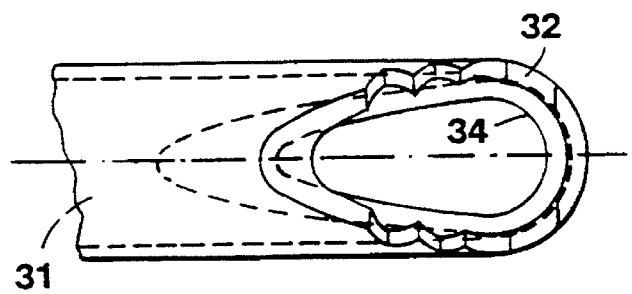
FIGS. 6 and 7 are top and side views, respectively, of the distal region of the intermediate tube of the surgical instrument.
Figure 7:
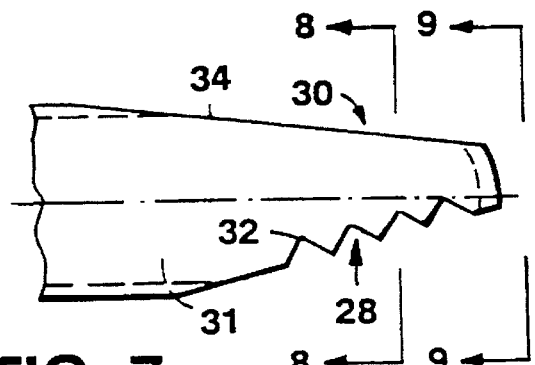
Figure 8:
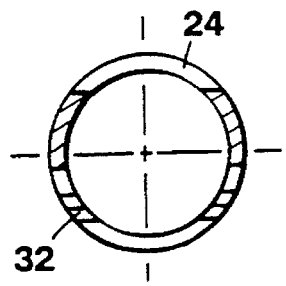
FIG. 8 is a sectional view of the distal region of the intermediate tube of the surgical instrument, taken along line 8—8 of FIG. 7.
Figure 9:
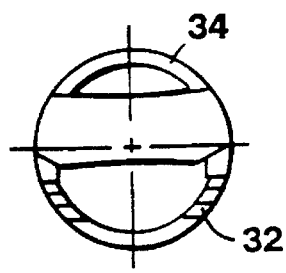
FIG. 9 is an end view of the distal region of the intermediate tube of the surgical instrument, taken along line 9—9 of FIG. 7.

As shown in FIGS. 1, 2, and 3, a surgical instrument 10 suitable for performing, e.g., closed, arthroscopic surgery on the knee with a surgical tool 12, includes an intermediate tube 14 within which a rotating inner tube 16 is coaxially disposed. In turn, intermediate tube 14 is coaxially disposed within a rotatable outer tube 18. Tubes 14, 16, and 18 extend distally from a base 20.

Referring also to FIG. 4, a distal region of outer tube 18 is partially cut away to form an aperture 22, which extends to the longitudinal axis 24 of instrument 10. The remaining, solid portion of the distal region of outer tube 18 comprises a shield 26. As outer tube 18 is rotated relative to intermediate tube 14, shield 26 alternately covers and uncovers an incisor window 28 and a synovator window 30 located on opposite sides of a window assembly 31 carried at the distal end of intermediate tube 14.

As shown in FIGS. 5-9, the edges 32 of incisor window 28 are sharpened and serrated, and the edges 34 of synovator window 30 are sharpened and smooth. Referring to FIG. 4, a window 35 formed by the sharpened, smooth edges 37 of a cutting implement 36 carried at the distal end of inner tube 16 is periodically exposed through incisor window 28 and synovator window 30 as inner tube 16 rotates. Thus, tissue entering through either incisor window 28 or synovator window 30 (depending on the rotational orientation of shield 26) can extend into the interior of inner tube 16. As inner tube 16 rotates, edges 37 of cutting implement 36 move toward and closely past edges 32, 34 of windows 28, 30 in window assembly 31, severing the tissue projecting therethrough. Together, cutting implement 36 and window assembly 31 comprise surgical tool 12.

Figure 10:
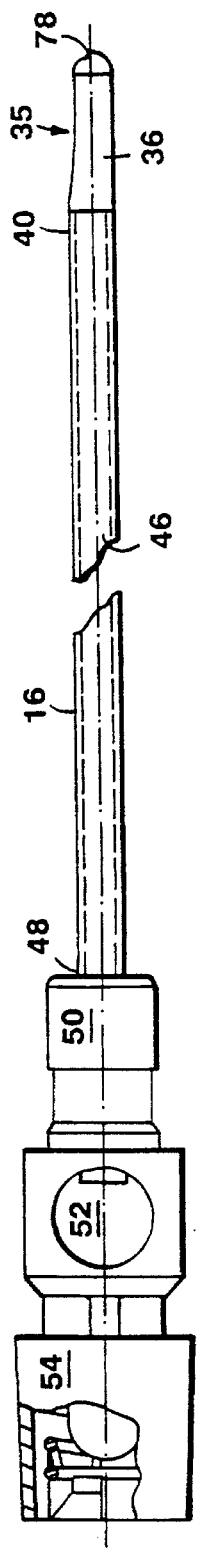
FIGS. 10, 11, and 12 show inner, intermediate, and outer tubes, respectively, of the surgical instrument.

Inner tube 16 is made from metal or other rigid material, such as stainless steel. As shown in FIG. 10, the distal end 40 of inner tube 16 supports cutting implement 36 (made from, for example, stainless steel and attached to tube 16 by welding or brazing). Cutting implement 36 is sized to provide a close-running fit with the inner portion of window assembly 31 for efficient cutting. The opening defined by window 35 in implement 36 is an extension of a central passage 46 in inner tube 16 that runs the entire length of tube 16.

Proximal region 48 of inner tube 16 is rigidly mounted to a drive shaft 50 that rotates within base 20, shown also in FIG. 2. Central passage 46 terminates in a vacuum source opening 52 in drive shaft 50. The proximal end 54 of drive shaft 50 fits into a handpiece 110 (Fig. 14), which includes a motor 112 for rotating drive shaft 50 and inner tube 16 with respect to both intermediate tube 14 and outer tube 18. One example of such a handpiece is described in U.S. Pat. No. 4,705,038, entitled "Surgical System for Powered Instruments", and assigned to the present assignee, which is incorporated by reference. Opening 52 is coupled to a vacuum source 114 (FIG. 14) during operation to remove severed tissue and irrigating fluid from the surgical site via passage 46, in a manner described in detail below.

Figure 11:
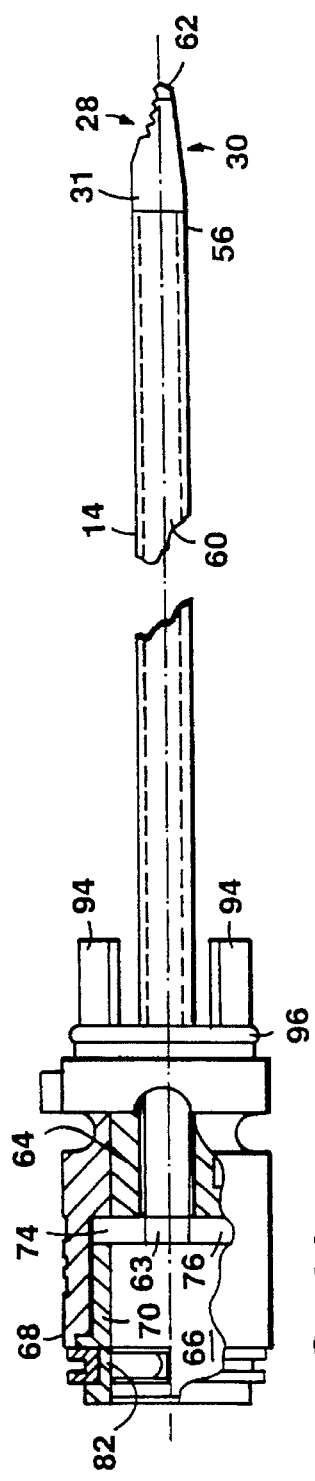

FIG. 11 shows intermediate tube 14, which is also made from a rigid material such as stainless steel or other metal. Distal end 56 of intermediate tube 14 supports window assembly 31 (made from, for example, stainless steel and attached to tube 14 by welding or brazing). The inner and outer diameters of window assembly 31 are substantially equal to the inner and outer diameters of tube 14.

Intermediate tube 14 is hollow along its entire length to provide a passage 60 that receives inner tube 16 and cutting implement 36, which extends to the partially closed distal end 62 of window assembly 31. The openings defined by windows 28, 30 in window assembly 31 are extensions of passage 60. The inner diameter of intermediate tube 14 is only slightly larger than the outer diameter of inner tube 16 (e.g., by approximately 0.002 inches, or 0.051 mm). This allows inner tube 16 to rotate freely but helps minimize wobbling of tube 16 to keep sharp cutting edges 37 of cutting implement 36 and edges 32, 34 of windows 28, 30 closely aligned.

The proximal end 63 of intermediate tube 16 is rigidly mounted to a coupling 64 located within a cavity 66 of a hub 68 of base 20, shown also in FIG. 2. Cavity 66 includes an axially extending keyway 70 sized and located to receive a key 74 on coupling 64. Thus, although coupling 64 can move axially with respect to hub 68, key 74 prevents coupling 64 from rotating.

Cavity 66 in hub 68 communicates with passage 60, and is configured to receive drive shaft 50. During assembly, after outer tube 18 has been attached to hub 68 in the manner described below, inner tube 16 is inserted through hub 68 into passage 60 of intermediate tube 14. When the distal tip 78 of cutting implement 36 (FIG. 10) contacts the inner surface of the distal tip 62 of window assembly 31, coupling 64 and intermediate tube 14 are forced distally, until the outer surface of distal tip 62 contacts the inner surface of the partially closed distal tip 80 of outer tube 18. Thus, because intermediate tube 14 can slide axially with respect to hub 68, the gap between the distal tips of intermediate tube 14 and outer tube 18, as well as the gap between the distal tips of inner tube 16 and intermediate tube 14, are essentially zero. This reduces the amount of severed tissue, fluid, and other material that would otherwise pass into the annular regions separating tubes 14, 16, 18. With inner tube 16 installed, a pliable fitting 82 retains drive shaft 50 within hub 68. Fitting 82 provides a fluid-tight seal when base 20 is inserted into handpiece 110.

Figure 12:
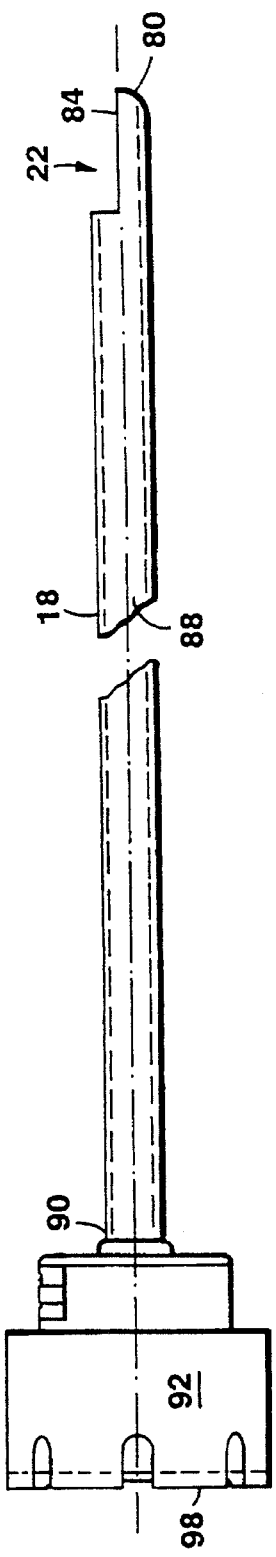

Outer tube 18, shown in FIG. 12, is also made from a rigid material such as stainless steel or other metal. Aperture 22 is defined by smooth, unsharpened edges 84 of tube 18. Edges 84 extend, parallel to axis 24, from a point proximal of the distal tip 80 to distal tip 80. Aperture 22 is an extension of a central passage 88 in outer tube 18 that runs the entire length of tube 18.

Proximal region 90 of outer tube 18 is rigidly mounted to a knob 92 that rotatably couples to hub 68 of base 20. As shown in FIG. 11, a pair of fingers 94 extends distally from base 68, parallel to axis 24, and a raised shoulder region 96 encircles base 68 immediately proximal of the point where fingers 94 attach to base 68. When intermediate tube 14 is inserted into passage 88 of outer tube 18 and knob 92 and base 20 are forced together, a mating shoulder 98 on the inner surface of the proximal end of knob 92 engages shoulder 96, as shown in FIG. 2, preventing knob 92 and base 68 from separating longitudinally.

Figure 13:
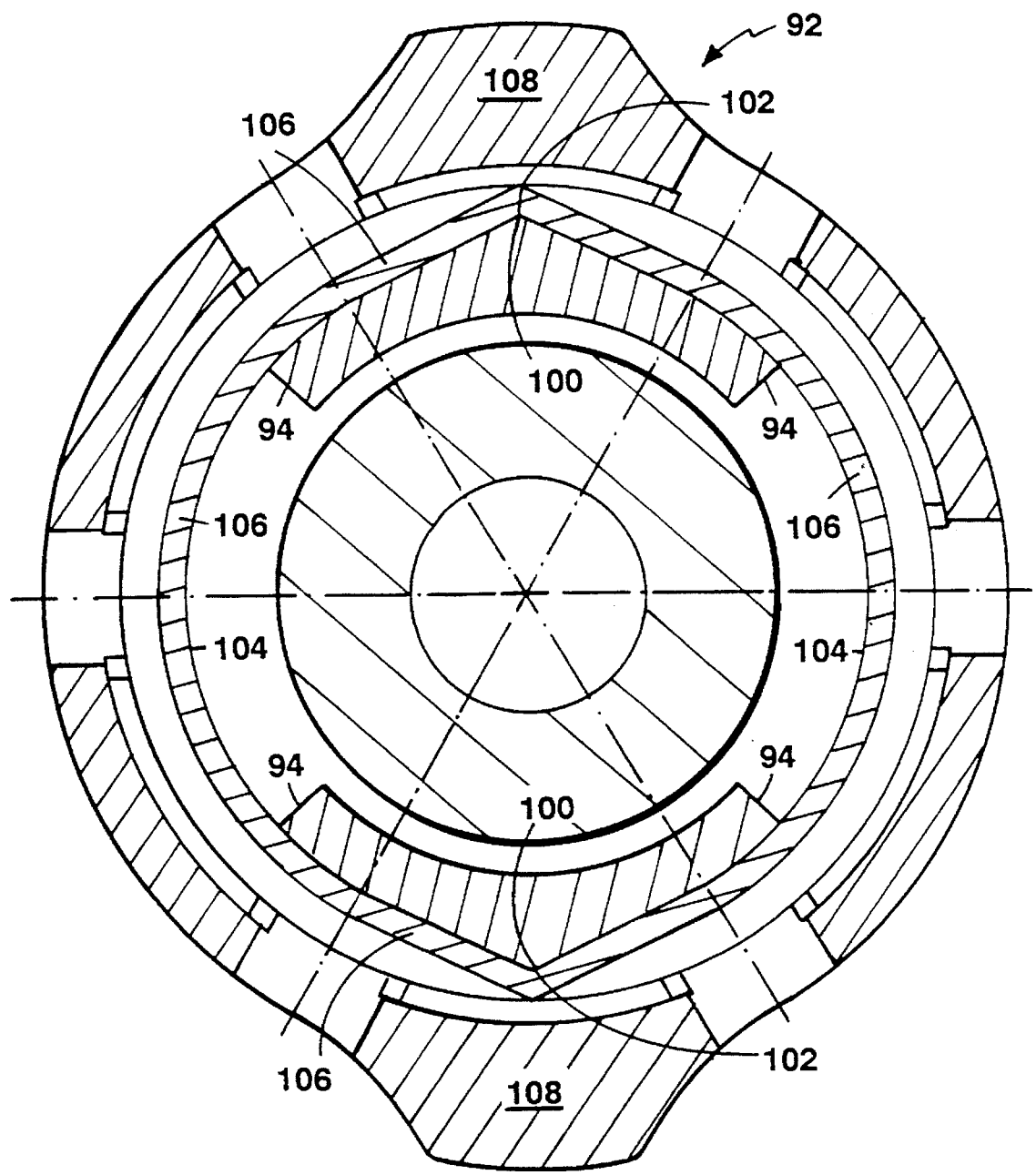
FIG. 13 is a sectional view of a ratchet mechanism of the surgical instrument, taken along line 13—13 of FIG. 1.

As shown in FIG. 13, fingers 94 are quasi-pentagonal in cross-section. With knob 92 installed, the radial outermost point 100 of each finger 94 rests in an a mating apex 102 on the inner surface of knob 92. Apexes 102 are formed by the intersection of adjacent arcuate surfaces 104 of a wall 106 of knob 92. Fingers 94 and arcuate surfaces 104 coact to allow the relative rotational orientation between knob 92 and hub 68 to be changed, in a ratchet-like fashion, in discrete, 180° steps. In particular, outer tube 18, knob 92, and fingers 94 are oriented so that incisor window 28 is fully covered by shield 26 when knob 92 is rotated to one step, and synovator window 30 is fully covered by shield 26 when knob 92 is rotated to the other step.

As knob 92 is rotated with respect to hub 68, outermost points 100 move across arcuate surfaces 104, initially forcing fingers 94 radially inward. When outermost points 100 move past the respective midpoints of surfaces 104, the elastic energy stored in the displaced flexible fingers 94 forces the fingers radially outward until the relative rotational orientation between knob 92 and hub 68 has changed by 180°, and fingers 98 rest in the opposite apex 102. Thus, fingers 94 positively urge outermost points 100 into each associated apex as it is encountered, thereby giving the surgeon kinesthetic feedback as to the amount by which outer tube 18 has been rotated, and also helping to avoid accidental rotation of outer tube 18 with respect to windows 28, 30. Moreover, a pair of diametrically opposed bulges 108 on the outer surface of knob 92 are oriented adjacent to, and at the same circumferential location as, apexes 102. Bulges 108 thus make knob 92 easier to grasp, and further indicate to the surgeon when knob 92 has been rotated a sufficient degree. Together, fingers 94 and knob 92 comprise a ratchet assembly.

Figure 14:
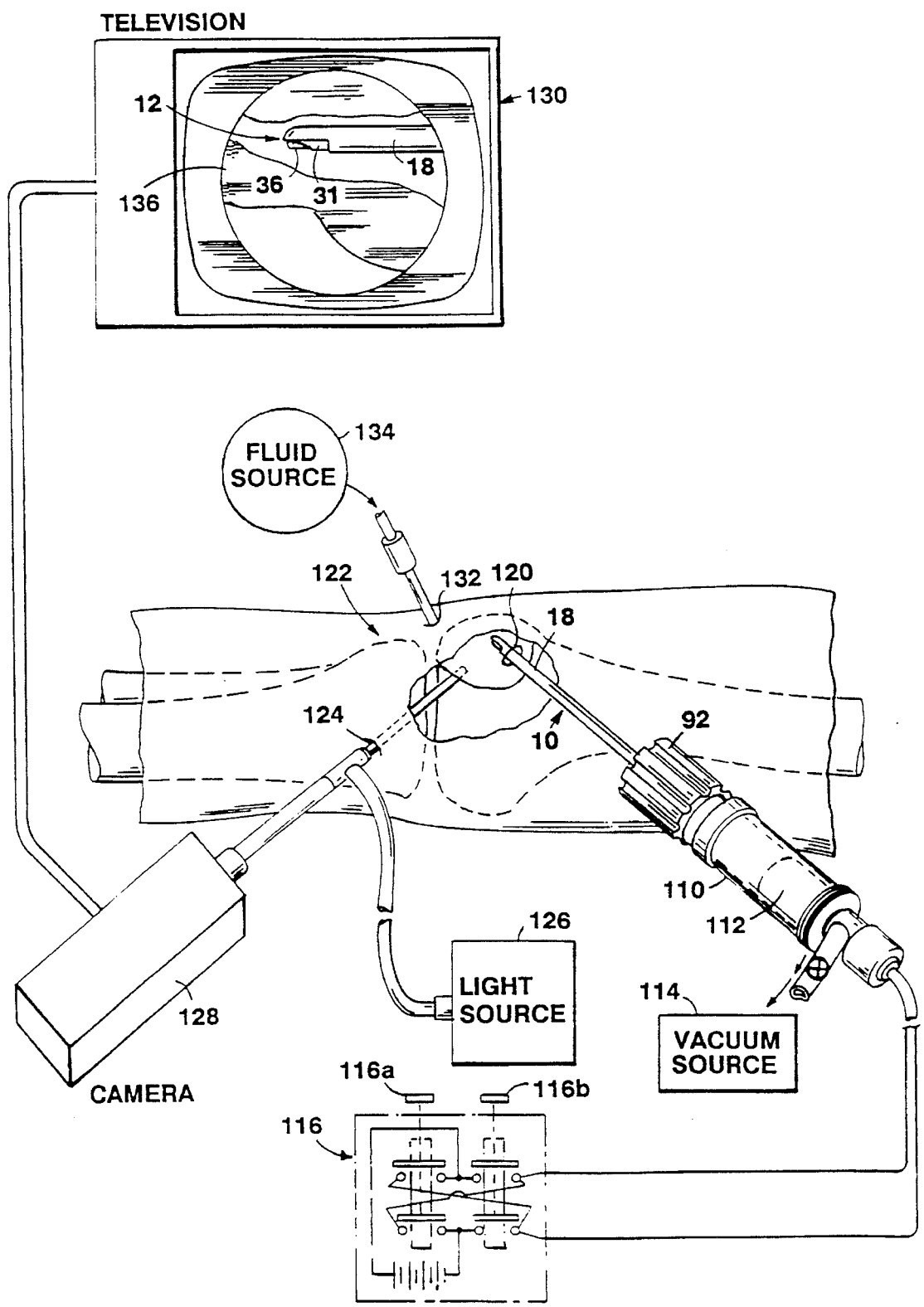
FIG. 14 shows the surgical instrument in use.

Referring also to FIG. 14, in operation, surgical instrument 10 is inserted into the distal end of a handpiece 110. Outer tube 18 is then introduced as shown through a puncture wound 120 into the knee joint 122, below the patella. Light is projected into the joint via a second puncture 124 using a fiber optic light source 126, and a visual image of the surgical site is returned through a separate optical path to a television camera 128. The image is delivered by camera 128 onto a television screen 130 for viewing by the surgeon. (Alternatively, the surgeon can view the image using an eyepiece, or the image can be recorded.)

The surgeon operates surgical tool 12 by activating motor 112, which receives operating potential and current from power supply 116. Motor 112 engages and rotates drive shaft 50, thereby applying rotational force to inner tube 16 and rotating tube 16 with respect to tubes 14, 18. The surgeon controls rotational speed and direction (either unidirectional or oscillatory) using foot switches 116a, 116b, which control the magnitude and polarity of operating potential and current provided by power supply 116 to motor 112. Motor 112 is capable of rotating inner tube 16 over a wide range of speeds, e.g., between about 100 rpm and 5000 rpm, and can deliver a torque of up to 25 oz. inches (0.177 Nm).

Different types of surgical instruments such as instrument 10 have rotational and torsional limits. To prevent the surgeon from inadvertently operating instrument 10 at dangerously high speeds and torques, instrument 10 identifies to sensors (not shown) in handpiece 110 what type of instrument it is, and the speed of and torsion applied by motor 112 is controlled so that these limits are not exceeded. (This control technique is described in the aforementioned U.S. Pat. No. 4,705,038.)

During the surgical procedure, the body joint is distended with fluid introduced through a third puncture wound 132 from a fluid source 134. The fluid irrigates the site and renders tissue 136 (which is, e.g., synovial tissue) mobile so that it floats and can be displaced (similar to the movement of seaweed in water).

The surgeon progressively cuts away synovial tissue 136 by moving surgical instrument 10 from side to side and in the axial direction using handpiece 110 (while viewing television screen 130). For instance, if incisor window 28 is exposed to the joint tissue (that is, if synovator window 30 is fully covered by shield 26), instrument 10 will cut tissue aggressively, because of the configuration of serrated edges 32. If during the procedure the surgeon desires instead to cut tissue less aggressively, the present invention allows him to do so simply by holding knob 92 fixed, and rotating handpiece 110 (and thus hub 68) until incisor window 28 is fully covered by shield 26. This exposes the less-aggressive, smooth-edged synovator window 30. The ratchet mechanism provides the surgeon with kinesthetic feedback, indicating when the handpiece 110 has been rotated the requisite 180°. (Alternatively, handpiece 110 can be held fixed and knob 92 rotated. Because incisor window 28 is located on the opposite side of window assembly 31 from synovator window 30, in order to resume cutting the same tissue as before, the surgeon would then rotate instrument 10 180° about axis 24.)

The surgeon can change the rotational orientation of shield 26 with respect to windows 28, 30 at any time. For example, inner tube 16 can be driven by motor 112 or may be stationary while the surgeon rotates shield 26. The surgeon can resume more aggressive tissue-cutting at any time simply by rotating knob 92 or handpiece 110 in either direction.

Tissue fragments and other body material cut by surgical tool 12 are withdrawn from the surgical site along with irrigation fluid via central passage 46 of inner tube 16 (FIGS. 2, 10) in response to suction applied by vacuum source 114.

Other embodiments are within the scope of the following claims.

Figure 15:
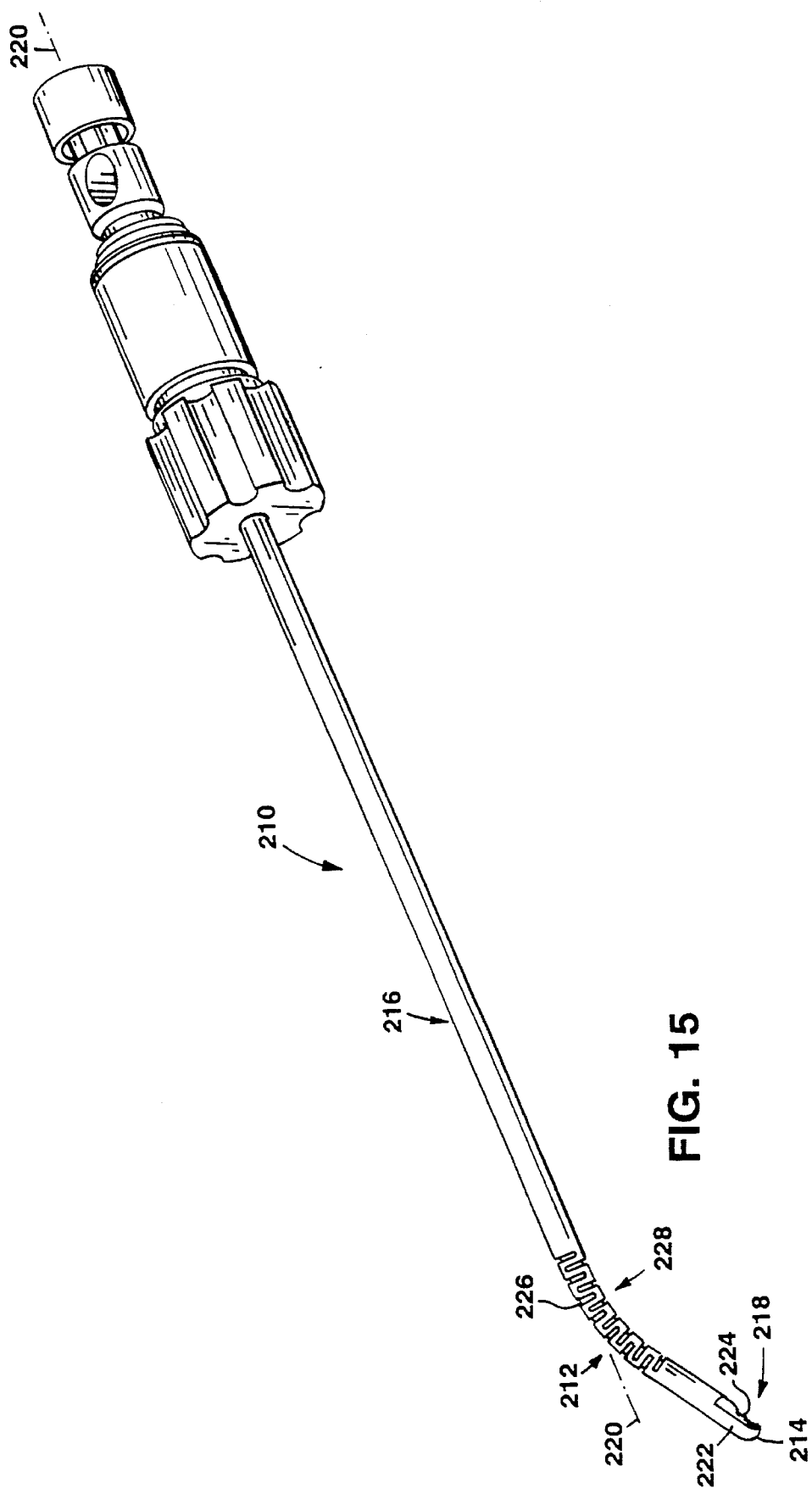
FIG. 15 shows another embodiment of a surgical instrument.

For example, although surgical instrument 10 is straight between its proximal and distal ends, a surgical instrument 210 embodying the teachings disclosed herein could instead include a bend region 212, as shown in FIG. 15. Bend region 212, which is disposed slightly proximal of the distal end 214 of outer tube 216, angularly offsets surgical tool 218 from a generally straight axis 220 of surgical instrument 210. Bend region 212 enables surgical instrument 210 to operate on surgical areas that are difficult to reach with a straight-shafted instrument.

In order to rotate a shield 222 at a distal region of outer tube 216 to selectively cover and uncover an incisor window 224 and a synovator window (not shown) located on opposite sides of an assembly carried at the distal end of a bent, rigid intermediate tube 226, outer tube 216 is flexible at least in bend region 212. The inner tube (not shown) is likewise flexible at least in bend region 212, allowing it to transmit torque through bend region 212 to operate surgical tool 218. Alternatively, the intermediate and inner tubes may be flexible, and the outer tube may be rigid. In this latter embodiment, intermediate tube 226 is rotated to selectively cover and uncover the incisor and synovator windows, and outer tube 216 (and thus also shield 222) remains stationary. Similar flexible tube arrangements are disclosed in copending application Ser. No. 08/200,662, filed on Feb. 23, 1994, which is a continuation-in-part of application Ser. No. 08/011,364, filed on Jan. 29, 1993, which are both assigned to the present assignee and incorporated herein by reference in their entirety.

Various tube configurations exhibit the requisite flexibility at least in the bend region to be employed in surgical instrument 210. For instance, a region of an otherwise rigid tube or tubes may be relieved with a series of axially spaced, circumferentially extending slots 228 (only slots 228 in outer tube 216 shown in FIG. 15). Slotting a rotatable tube for flexibility and torque transmission is described in U.S. Pat. No. 5,152,744, assigned to the present assignee and incorporated herein by reference in its entirety. To prevent tissue fragments or other body material from catching on or passing through the slots in the inner tube, the slots can be covered with a pliable material such as silicone RTV or a heat-shrinkable polymeric sheath (not shown).

The flexible region or regions can instead be comprised of a series of discrete, interengaging segments, as disclosed in copending application Ser. No. 08/228,083, filed on Apr. 15, 1994, which is assigned to the present assignee and incorporated herein by reference in its entirety. Alternatively, the tubes can be comprised, at least in the bend region, of a flexible or elastomeric material, such as rubber, plastic, or other polymer.

Intermediate tube 226 is comprised of a material (e.g., stainless steel or other metal, ceramic, or plastic) sufficiently rigid to retain the shape and orientation of bend region 212 during normal surgical use of instrument 210. Although bend region 212 is often preformed during manufacture (e.g., by molding intermediate tube 226 to the desired shape or by bending it around a mandrel), if intermediate tube 226 is comprised at least in the bend region of a plasticly deformable material, bend region 212 can alternatively or additionally be preshaped or reshaped by the surgeon prior to or during the procedure to best match the contours and characteristics of the surgical site.

Figure 16:
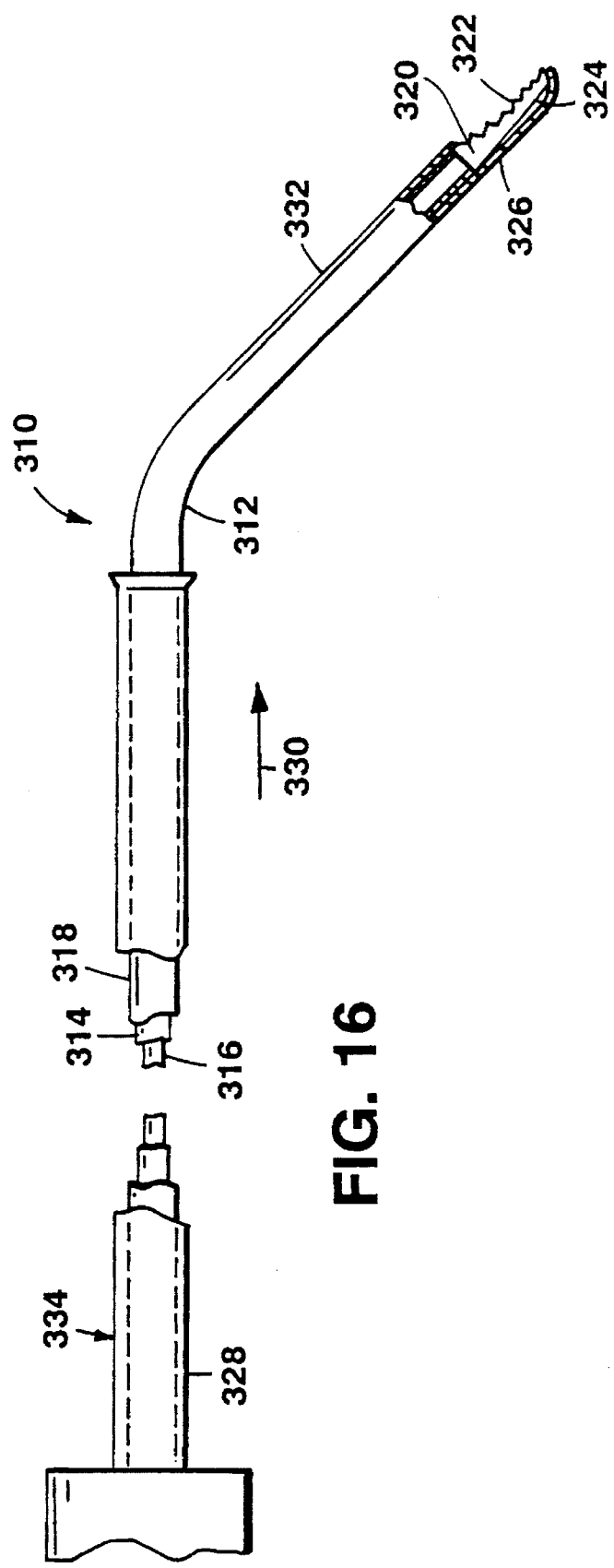
FIG. 16 shows another embodiment of a surgical instrument.

Another embodiment of the present invention, surgical instrument 310, is shown in FIG. 16. A bend region 312 in surgical instrument 310 is provided by a curved intermediate tube 314, and an inner tube 316 and an outer tube 318 of the instrument are flexible at least in bend region 312. (Alternatively, similar to the alternative embodiment described above in connection with FIG. 15, outer tube 318 could be curved, and intermediate tube 314 could be flexible at least in bend region 312.) A window assembly 320 carried at the distal end of intermediate tube 314 has oppositely disposed incisor and synovator windows 322, 324, within which a cutting implement (not shown) disposed at the distal end of inner tube 316 rotates. A shield 326 carried at the distal end of outer tube 318 can be rotated to selectively cover either of windows 322, 324.

Similar to the instrument disclosed in U.S. Pat. No. 5,282,821, incorporated herein by reference in its entirety, intermediate tube 314 of surgical instrument 310 is resilient, and a straight, rigid sheath 328 is disposed coaxially outside outer tube 318. Sheath 328 is axially slidable with respect to outer tube 318, and in its rest position (shown in FIG. 16) the distal end of sheath 328 terminates at a point just proximal of bend region 312. Sliding sheath 328 distally (i.e., in the direction indicated by arrow 330) over bend region 312 causes intermediate tube 314 to straighten out, decreasing the angle of offset provided by bend region 312. Sliding sheath 328 proximally back to its rest position allows bend region 312 to recover its preformed curvature. Thus, the angle of offset of the distal region 332 of instrument 310 with respect to the proximal region 334 of the instrument can be selectively changed while the instrument remains in situ within the patient.

Other types of surgical tools, such as abraders, may be employed with any of surgical instruments 10, 210, 310. Moreover, the surgical tool may be removably connected to the distal end of the inner tube, allowing just the surgical tool to be replaced should it become worn or damaged, as disclosed in U.S. Pat. No. 5,320,635, assigned to the present assignee and incorporated herein by reference in its entirety. Also, the surgical tool and the inner tube need not be comprised of the same material. Rather, the surgical tool will often be comprised of a hard material well-suited to cutting, whereas the inner tube may be comprised instead of a more compliant material (at least in the bend region) for transmitting torque through the bend region.

In addition, the inner, intermediate, and outer members need not be tubes, but could instead be, e.g., solid members or cables. Moreover, the proximal end of the outer member can be coupled to a source of rotational power, such as a motor (not shown), allowing the shield to be either power-rotated or manually actuated. Further, the intermediate tube of the instrument may be provided with more or fewer windows, and the window configurations may be tailored to different cutting applications. For instance, in some applications it may be useful to provide a single large window, and to vary the size of the window opening by partially covering it with the shield. In such an application, it might be desirable to remove the ratchet mechanism to allow knob 92 to rotate smoothly with respect to hub 68, or to modify the ratchet mechanism to rotate in smaller incremental steps.

In addition, the shield need not be attached to a member that extends from the base. Rather, the shield may be a cap mounted on the distal end of the intermediate tube. In such a construction, the instrument would have to be withdrawn from the joint space in order to select a different window for cutting. Also, the shield need not rotate, but could be configured instead to slide along the intermediate tube to selectively cover and uncover either or both of the windows. The inner member could likewise translate axially to operate the distal tip surgical tool.

While the invention has been described in terms of surgical instruments for arthroscopy, the invention may also be used with other types of instruments, for example, instruments configured for other kinds of endoscopic procedures and for biopsy applications.

What is claimed is:

1. A surgical instrument comprising:

a base;

a support member extending distally from said base and carrying at a distal region a window defining an opening;

a surgical tool at least partially disposed at said distal region of said support member and movable to cut tissue extending through said opening; and a shield rotatably mounted at said distal region of said support member so that said shield can be rotated with respect to said window to at least partially cover said opening.

2. The instrument of claim 1 further comprising a second window defining a second opening carried at said distal region of said support member.

3. The instrument of claim 2 wherein said shield is rotatable to selectively cover one of said opening and said second opening.

4. The instrument of claim 1 further comprising an actuating member extending distally from said base for transmitting a rotational force applied at a proximal end of said actuating member to rotate said shield with respect to said window to at least partially cover said opening.

5. The instrument of claim 4 wherein said actuating member comprises a tube.

6. The instrument of claim 1 wherein said support member is axially slidable with respect to said base.

7. The instrument of claim 1 wherein said support member comprises a tube.

8. The instrument of claim 1 wherein said window is defined in an assembly attached to a distal end of said support member.

9. The instrument of claim 1 further comprising a drive member extending distally from said base for transmitting a force applied at a proximal end of said drive member to move at least a portion of said surgical tool.

10. The instrument of claim 9 wherein said surgical tool comprises a cutting implement attached to a distal end of said drive member.

11. The instrument of claim 10 wherein edges of said cutting implement move toward and closely past edges of said window in response to said force transmitted by said drive member.

12. The instrument of claim 11 wherein said cutting implement rotates with respect to said window in response to a rotational force transmitted by said drive member.

13. The instrument of claim 12 wherein said drive member is hollow and is adapted to receive suction at its proximal end and to transport body material cut by said cutting implement away from a surgical site while the instrument remains in situ for further cutting.

14. The instrument of claim 9 wherein said drive member comprises a tube.

15. The instrument of claim 1 further comprising a bend region in said support member.

16. The instrument of claim 15 further comprising an actuating member extending distally from said base for transmitting a force applied at a proximal end of said actuating member through said bend region to rotate said shield, wherein said actuating member is relatively flexible at least in said bend region.

17. The instrument of claim 16 wherein said actuating member is a tube disposed outside said support member, and wherein said tube is relieved with a series of axially spaced slots in the area of said bend region to render said tube relatively flexible.

18. The instrument of claim 15 wherein said support member is relatively deformable at least in said bend region.

19. The instrument of claim 18 further comprising a rigid sheath disposed coaxially with and axially slidable with respect to said support member.

20. A surgical instrument comprising:

a base;

a support member extending distally from said base and carrying at a distal region a window defining an opening;

a surgical tool at least partially disposed at said distal region of said support member and movable to cut tissue extending through said opening;

a shield mounted at said distal region of said support member; and an actuating member extending distally from said base for transmitting a force applied at a proximal end of said actuating member to move said shield with respect to said window to at least partially cover said opening, said proximal end of said actuating member being rigidly secured to a knob rotatably mounted to a stationary portion of said base.

21. The instrument of claim 7 wherein said knob is mounted to said stationary portion so that said knob can be selectively rotated to a plurality of discrete positions with respect to said stationary portion, thereby to allow said shield to be selectively positioned to a corresponding plurality of discrere rotational orientations.

22. A surgical instrument comprising:

a base;

a support member extending distally from said base and carrying at a distal region a first window and a second window defining respective first and second openings;

a surgical tool at least partially disposed at said distal region of said support member and movable to cut tissue extending through said openings; and a shield mounted at said distal region of said support member and movable with respect to said windows to selectively cover one of said openings.

23. The instrument of claim 22 wherein said shield is movable to at least partially cover one of said openings.

24. The instrument of claim 22 wherein said first window is configured for more aggressive cutting than said second window.

25. A surgical instrument comprising:

a base;

a first tube extending distally from said base and carrying at a distal region a first window and a second window defining respective first and second openings;

a second tube disposed coaxially within said first tube and rotatably mounted with respect to said base, said second tube carrying a surgical tool in said distal region to cut tissue extending through said openings when said second tube is rotated with respect to said first tube; and a third tube disposed coaxially outside said first tube and rotatably coupled to said base, said third tube carrying a shield in said distal region to selectively cover one of said openings when said third tube is rotated with respect to said first tube.

26. A method of surgery for a joint space comprising:

providing a surgical instrument comprising:

a base;

a support member extending distally from said base and carrying at a distal region a window defining an opening;

a surgical tool at least partially disposed at said distal region of said support member and movable to cut tissue extending through said opening; and a shield rotatably mounted at said distal region of said support member;

introducing said surgical instrument into said joint and applying a force at a proximal end of said surgical device to operate said surgical tool to cut tissue of the joint exposed to said surgical tool through said opening; and rotating said shield with respect to said window to at least partially cover said opening.

27. The method of claim 26 further comprising the step of rotating said shield with respect to said window to completely cover said opening.

28. The method of claim 26 further comprising providing said surgical instrument with a second window defining a second opening carried at said distal region of said support member, and rotating said shield to selectively cover one of said opening and said second opening.

29. A surgical instrument comprising:

a base;

a support member extending distally from said base and carrying at a distal region a window defining a side-facing opening;

a surgical tool at least partially disposed at said distal region of said support member and movable with respect to an edge of said side-facing opening to cut tissue extending through said opening;

a shield mounted at a distal end of said support member; and an actuating member extending distally from said base for transmitting a force applied at a proximal end of said actuating member to move said shield with respect to said window to at least partially cover said side-facing opening.

30. The instrument of claim 29 further comprising a second window defining a second opening carried at said distal region of said support member, wherein said shield is movable by said actuating member to selectively cover one of said opening and said second opening.

* * * * *

UNITED STATES PATENT AND TRADEMARK OFFICE
CERTIFICATE OF CORRECTION

PATENT NO. : 5,601,583

DATED : February 11, 1997

INVENTOR(S) : John R. Donahue et al.

It is certified that error appears in the above-identified patent and that said Letters Patent is hereby corrected as shown below:

Col. 10, claim 21, line 23, replace "claim 7" with --claim 20--.

Col. 10, claim 21, line 28, replace "discrere" with --discrete--.

Signed and Sealed this

Fourteenth Day of October, 1997

*Attest:*

BRUCE LEHMAN

*Attesting Officer*     *Commissioner of Patents and Trademarks*